(12) United States Patent
Radtke

(10) Patent No.: US 6,391,298 B1
(45) Date of Patent: May 21, 2002

(54) METHOD OF USING PON-1 TO DECREASE ATHEROMA FORMATION

(75) Inventor: Klaus-Peter Radtke, Apex, NC (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/199,672

(22) Filed: Nov. 25, 1998

(51) Int. Cl.$^7$ .......................... A61K 38/46; C12N 9/16; C12N 1/20; C07K 21/04; C07K 16/00
(52) U.S. Cl. ................... 424/94.6; 435/196; 435/252.3; 435/320.1; 536/23.2; 530/350; 530/387.1
(58) Field of Search ................... 424/94.6; 435/196, 435/252.3, 320.1; 536/23.2; 530/387.1, 350

(56) References Cited

U.S. PATENT DOCUMENTS 5,629,193 A    5/1997   Hudson et al. ............. 435/325

FOREIGN PATENT DOCUMENTS

WO         9601322        1/1996

OTHER PUBLICATIONS

Adkins, S., Gan, K. N., Mody, M., and La Du, B. T., "Molecular Basis for the Plymorphic Forms of Human Serum Paraoxonase/Arylesterase: Glutamine or Arginine at Position 191, for the Respective A or B Allozymes", Am. J. Hum. Genet. 52: 598–608 (1993).

Aviram, M., Rosenblat, M., Bisgaier, C. L., Newton, R. S., Primo–Parmo, S. L., and La Du, B. N., "Paraoxonase Inhibits High–density Lipoprotein Oxidation and Preserves its Functions. A Possible Peroxidative Role for Paraoxonase", J. Clin. Invest. 101(8): 1581–1590 (Apr. 1998).

Blatter, M–C., James, R. W., Messmer, S., Barja, F., and Pometta, D., "Identification of a distinct human high–density lipoprotein subspecies defined by a lipoprotein–associated protein, K-45. Identity of K-45 with paraoxonase", Eur. J. Biochem. 211: 871–879 (1993).

Blatter Garin, M–C., James, R. W., Dussoix, P., Blanche, H., Passa, P., and Froguel, P., "Paraoxonase Polymorphism Met–Leu54 is Associated with Modified Serum Concentrations of the Enzyme", J. Clin. Invest. 99(1): 62–66 (Jan. 1997).

Chemnitius, J., Losch, H., Losch, K., and Zech, R., "Organophosphate Detoxicating Hydrolases in Different Vertebrate Species", Comp. Biochem. Physiol 76C: 85–93 (1983).

Eckerson, H. W., Wyte, C. M., and La Du, B. N., "The Human Serum Paraoxonase/Arylesterase Polymorphism", Am. J. Hum. Genet. 35: 1126–1138 (1983).

Ikeda, Y., Suehiro, T., Inoue, M., Nakauchi, Y., Morita, T., Arii, K., Ito, H., Kumon, Y., and Hashimoto, K., "Serum Paraoxonase Activity and its Relationship to Diabetic Complications in Patients with Non–Insulin–Dependent Diabetes Mellitus", Metabolism 47(5): 598–602 (May 1998).

Kelso, G. J., Stuart, W. D., Richter, R. J., Furlong, C. E., Jordan–Starck, T. C., and Harmony, J. A. K., "Apolipoprotein J is Associated with Paraoxonase in Human Plasma", Biochemistry 33: 832–839 (1994).

Leviev, I., Negro, F., and James, R. W., "Two Alleles of the Human Paraoxonase Gene Produce Different Amounts of mRNA. An Explanation for Differences in Serum Concentrations of Paraoxonase Associated with the (Leu–Met54) Polymorphism", Arteriosclerosis, Thrombosis, and Vascular Biology 17(11):2935–2939 (Nov. 1997).

Li, W. F. , Furlong, C. E. and Costa, L. G., "Paraoxonase Protects Against Chlorpyrifos Toxicity in Mice", Toxicology Letters 76: 219–226 (1995).

Li, W., Costa, L. G., and Furlong, C. E., "Serum Paraoxonase Status: A Major Factor in Determining Resistance to Organophosphates", J. Toxicology and Environmental Health 40: 337–346 (1993).

Lorentz, K., Flatter, B., and Augustin, E., "Arylesterase in Serum: Elaboration and Clinical Application of a Fixed–Incubation Method", Clin. Chem. 25(10): 1714–1720 (1979).

Losch, H., Losch, K., Haselmeyer, K. H., Chemnitius, J. M., and Zech, R., "Die Enzymatische Entgiftung von Phosphororganischen Insektiziden und Nervengasen in Primaten", Arzneim.–Forsch./Drug REs. 32(II), Nr. 12: 1523–1529 (1982).

Mackness, B., Durrington, P. N., and Mackness, M. I., "Human Serum Paraoxonase", Gen. Pharmacol. 31(3): 329–336 (1998).

Mackness, M. I., Mackness, B., Durrington, P. N., Fogelman, A. M., Berliner, J., Lusis, A. J., Navab, M., Shih, D., and Fonarow, G. C., "Paraoxonase and coronary heart disease", Curr. Opin. Lipidol. 9(4): 319–324 (1998).

Mackness, M. I., Mackness, B., Arrol, S., Wood, G., Bhatnagar, D., and Durrington, P. N., "Presence of paazoxonase in human interstitial fluid", Febs Letters 416: 377–380 (1997).

Mackness, M. I., and Durrington, P. N., "HDL, its enzymes and its potential to influence lipid peroxidation", Atherosclerosis 115: 243–253 (1995).

(List continued on next page.)

*Primary Examiner*—Tekchand Saidha
(74) *Attorney, Agent, or Firm*—Womble Carlyle Sandridge & Rice, PLLC

(57) ABSTRACT

The invention is directed to a method of decreasing atheroma formation in a mammal comprising administering a pharmaceutically effective amount of PON-1 or its functional equivalent to a patient in need thereof. Also included herein are pharmaceutical compositions, and a method for diagnosing predisposition to hypercholesterolemia by assessing the level of native circulating PON-1.

11 Claims, 4 Drawing Sheets

OTHER PUBLICATIONS

Mackness, M. I., and Durrington, P. N., "Paraoxonase: Another Factor of NIDDM Cardiovascular Disease", The Lancet, 346: 856 (Sep. 30, 1995).

Mackness, M. I., Arrol, S., Abbott, C., and Durrington, P. N., "Protection of low–density lipoprotein against oxidative modification by high–density lipoprotein associated paraoxonase", Atherosclerosis 104: 129–135 (1993).

Mackness, M. I., Arrol, S., Abbott, C. A., and Durrington, P. N., "Is Paraoxonase Related to Atherosclerosis", Chem. Biol. Interactions 87: 161–171 (1993).

Mackness, M. I., Harty, D., Bhatnagar, D., Winocour, P. H., Arrol, S., Ishola M., and Durrington, P. N., "Serum paraoxonase activity in familial hypercholesterolaemia and insulin–dependent diabetes mellitus", Atherosclerosis 86: 193–199 (1991).

Mackness, M. I., Arrol, S., and Durrington, P. N., "Paraoxonase Prevents Accumulation of Lipoprotein of Lipoperoxides in Low–density Lipoprotein", Febs Letters 286(1–2): 152–154 (Jul. 1991).

Main, A. R., "The Role of A–Esterase in the Acute Toxicity of Paraoxon, Tepp, and Parathion", Can. J. Biochem. Physiol. 34: 197–215 (1956).

Masson, P., Josse, D., Lockridge, O., Viguié, N., Taupin, C., and Buhler, C., "Enzymes hydrolyzin organophsphates as potential catalytic scavengers against organophosphate poisoning", J. Physiology (Paris) 92: 357–362 (1998).

Mochizuki, H., Scherer, S. W., Xi, T., Nickle, D. C., Majer, M., Huizenga, J. J., Tsui, L–C., and Proschazka, M., "Human PON2 gene at 7q21.3: cloning, multiple mRNA forms, and missense polymorphisms in the coding sequence", Gene 213: 149–157 (1998).

Navab, M., Hama–Levy, S., Van Lenten, B. J., Fonarow, G. C., Cardinez, C. J., Castellani, L. W., Brennan, M–L., Lusis, A. J., and Fogelman, A. M., "Mildly Oxidized LDL Induces and Increased ApolipoproteinJ/Paraoxonase Ratio", J. Clin. INvest. 99(8): 2005–2019 (Apr. 1997).

Parthasarathy, S., Barnett, J., and Fong, L. G., High–densitiy lipoprotein inhibits the oxidative modification of low–density lipoprotein, Biochimica et Biophysica Acta 1044: 275–183 (1990).

Ruiz, J., James, R., Blatter Garin, M–C., Passa P., and Froguel, P., "Paraoxonase/Arylesterase Gene (Met–Leu55) Polymorphism is Independently Associated with Coronary Hear Disease in NIDDM", Complications, Macrovascular I, pp. 65A, #233.

Ruiz, J., Blanche, H., Blatter Garin, M–C., James, R., Passa, P., and Froguel, P., "Paraoxonase Gene Mutation (Gln–Arg19) in Coronary Heart Disease", Complications, Macrovascular, pp. 35A, #127.

Ruiz J., Blanche, H., James, R. W., Blatter Garin, M–C., Vaisse, C., Charpentier, G., Cohen, N., Morabia, A., Passa, P., and Froguel, P., "Gln–Arg192 polymorphism of paraoxonase and coronary heart disease in type 2 diabetes", The Lancet, 346: 869–872 (Sep. 30, 1995).

Sanghera, D. K., Saha, N., Aston, C. E., and Kamboh, M. I., "Genetic Polymorphism of Paraoxonase and the Risk of Coronary Heart Disease", Arteriosclerosis, Thrombosis, and Vascular Biology 17(6): 1067–1073 (Jun. 1997).

Schiavon, R., De Fanti, E., Giavarina D., Biasioli, S., Cavalcanti, G., and Guidi, G., "Serum paraoxonase activity is decreased in uremic patients", Clinica Chimica Acta 247: 71–80 (1996).

Serrato, M., and Marian A. J., "A Variant of Human Paraoxonase/Arylesterase (HUMPONA) Gene is a Risk Factor for Coronary Artery Disease", J. Clin. Invest. 96: 3005–3008 (Dec. 1995).

Shih, D. M., Gu, L., Xia, Y–R., Navab, M., Li, W–F., Hama, S., Castellani, L. W., Furlong, C. E., Costa, L. G., Fogelman, A. M., and Lusis, A. J., "Mice lacking serum paraoxonase are susceptible to organophosphate toxicity and atherosclerosis", Nature 394: 284–287 (Jul. 1998).

Shih, D. M., Gu, L., Hama, S., Xia, Y–R., Navab, M., Fogelman, A. M., and Lusis, A. J., "Genetic–Dietary Regulation of Serum Paraoxonase Expression and its Role in Atherogenesis in a Mouse Model", J. Clin. Invest. 97(7): 1630–1639 (Apr. 1996).

Szabo, I., Rona, K., Czinner, A., Gachalyi, B., and Kaldor A., "Is Paraoxon Hydrolytic Activity in Serum Predictive of Myocardial Infarction?", Clin. Chem. 33(5): 742–743 (May 1987).

Van Lenten, B. J., Hama, S. Y., De Beer, F. C., Stafforini, D. M., McIntyre, T. M., Prescott, S. M., La Du, B. N., Fogelman, A. M., and Navab, M., "Anti–inflammatory HDL Becomes Pro–inflammatory during the Acute Phase Response. Loss of Protective Effect of HDL against LDL Oxidation in Aortic Wall Cell Cocultures", J. Clin. Invest. 96: 2758–2767 (Dec. 1995).

Watson, A. D., Berliner, J. A., Hama, S. Y., La Du, B. N., Faull, K. F., Fogelman, A. M., and Navab, M., "Protective Effect of High Density Lipoprotein Associated Paraoxonase. Inhibition of the Biological Activity of Minimally Oxidized Low Density Lipoprotein", J. Clin. Invest. 96: 2882–2891 (Dec. 1995).

METHOD OF USING PON-1 TO DECREASE ATHEROMA FORMATION

BACKGROUND

1. Field of the Invention

The invention relates generally to the field of heart disease and cardiovascular disease. More specifically, the invention is directed to a method of decreasing atheroma formation in mammals, by administration of paraoxonase-1 (PON-1), an expressed protein that has hydrolase activity for organophosphates, and antioxidation activity for low-density lipoprotein (LDL).

2. Background

It is by now well-accepted that atherogenesis and hyperlipidemia are intimately related. Atherogenesis involves the build-up of cholesterol within the endothelium of arterial walls and the subsequent formation of placques. Placques can fissure, ultimately causing thrombus formation which may lead to stroke or myocardial infarction. Of the two forms of lipoproteins, high-density (HDL) and low-density lipoprotein (LDL), LDL is positively correlated with placque formation, while HDL is thought to be anti-atherogenic through the reverse cholesterol transport mechanism (see below).

The lipid transport system is divided into two major pathways, the exogenous pathway (dietary triglycerides and cholesterol absorbed by the intestine) and the endogenous pathway (triglycerides and cholesterol secreted by the liver). The reverse cholesterol transport system, mediated by HDL, is involved in both pathways and is thought to be a major non-receptor based mechanism for removal of cholesterol by HDL. Two subsets of HDL are involved in reverse cholesterol transport, HDL2 and HDL3. Nascent HDL accumulates cholesterol from cell membranes. The circulating enzyme lecithin-cholesterol acyltransferase ("LCAT") associates with HDL and esterifies free cholesterol, causing the esterified cholesterol to move into the core. HDL3 particles accumulate cholesteryl ester, and as it accumulates HDL3 becomes HDL2, which is rich in cholesteryl ester. The cholesteryl ester in HDL2 is then exchanged for triglyceride with the aid of cholesteryl ester transfer protein, converting HDL2 back to HDL3, which is then able to accumulate more free cholesterol. HDL is thought to be antiatherogenic through the reverse cholesterol transport system, because of its ability to take up excess free cholesterol.

Oxidation of LDL is a key intermediate in the formation of atherogenic placques. It has been found that LDL must undergo modification before it can be ingested by macrophages to form foam cells, which are important components of atherosclerotic placques (Steinberg, D., et al., "Beyond cholesterol: modifications of low-density cholesterol that increase its atherogenicity," *N. Engl. J. Med.* 320:915 (1989)). In vivo, oxidation is probably the most frequent form of LDL modification. Oxidized LDL not only contributes to the formation of foam cells, but also is chemotactic for circulating monocytes, is cytotoxic, and impairs endothelial function.

HDL was found to inhibit LDL oxidation, which is another potential mechanism by which HDL may reduce atherosclerosis. S. Parthasarathy and coworkers have shown that incubation of HDL with oxidatively-modified LDL results in inhibition of production of thiobarbituric acid-reactive products (TBARS) (Parthasarathy, S. et al., "High-density lipoprotein inhibits the oxidative modification of low-density lipoprotein," *Biochim. Biophys. Acta* 1044:275 (1990)). However, the mechanism for HDL's antioxidative function remains unknown. In another study, Klimov et al. injected 200 mg of human $HDL_3$ into rabbits which had been rendered hypercholesterolemic by cholesterol feeding. Total plasma conjugated dienes and trienes were reduced by 20–30% six hours after the injection and remained at that reduced level up to twenty-four hours after the injection (Klimov, A. N., et al., "Antioxidative activity of high density lipoproteins in vivo," *Atherosclerosis* 100:13 (1993)).

Antioxidant therapy has been shown to improve endothelial cell function in patients with hypercholesterolemia and coronary artery disease (Anderson, T J, et al., "The effect of cholesterol-lowering and antioxidant therapy on endothelium-dependent coronary vasomotion," *N. Engl. J. Med.* 332:488 (1995)). The Cambridge Heart Antioxidant Study (CHAOS) randomized 2,002 patients with proven coronary disease to vitamin E, 400 to 800 I.U., or placebo. After a median follow-up of 1.4 years, antioxidant treatment reduced the primary endpoint of cardiovascular death and nonfatal MI by 47 percent (41 v. 64 events) (Stephens, N. G., et al., "Randomized controlled trial of Vitamin E in patients with coronary disease: Cambridge Heart Antioxidant Study (CHAOS)," *Lancet* 347:781 (1996)).

Paraoxonase (PON) is a protein secreted by the liver that is found primarily in serum. The name is derived from its ability to hydrolyze the organophosphate paraoxon in vivo. There are 3 known allelic forms of PON. Serum paraoxonase/arylesterase (PON-1) is a 354 residue 43–45 kDa A-esterase associated with HDL (Kelso, G. J., et al., "Apolipoprotein J is associated with paraoxonase in human plasma," *Biochemistry* 33: 832–839 (1994)). It is well-known to be involved in the hydrolysis of several organophosphate insecticides (Murphy, S. D. in *Toxicology: The Basic Science of Poisons,* (eds. Doull, J., Klassen, C., & Amdur, M.) 357–408, Macmillan, New York, (1980); Tafuri, J., et al., "Organophosphate poisoning," *Ann. Emerg. Med.* 16:193–202 (1987)). PON2 and PON3 are known allelic variants that have similar sequences. It is not known if PON2 or PON3 are expressed in vivo. U.S. Pat. Nos. 5,792,639 and 5,629,193 (Human Genome Sciences) are directed to a human paraoxonase gene, its associated vectors and transformed host cells and their use to detoxify organophosphates in vivo and for a neuroprotective effect. The DNA sequence claimed by HGS is likely that of PON2 based on homology searching. An alignment of the PON1 and PON2 nucleic acid sequences shows 69% identity. There is no suggestion in either the '639 or the '193 patents for the use of paraoxonase to reduce atheroma formation described herein.

The physiologic activity of the PON family members was, until recently, unknown. It has recently been postulated that PON may play a role as an in vivo antioxidant that may reduce the peroxidation of LDL (Mackness, M. I., et al., "HDL, its enzymes and its potential to influence lipid peroxidation," *Atherosclerosis* 115:243–253 (1995)). However, the same review stated that other enzymes resident on HDL may also play the same role, such as platelet activating factor acetylhydrolase (Stafforini, D. M., et al., "The plasma PAF acetylhydrolase prevents oxidative modification of low density lipoprotein," *J. Lipid Mediators Cell Signaling* 10:53 (1994)).

Several human population studies have revealed significant associations between the common polymorphisms of the PON1 gene and coronary artery disease (CAD) (Ruiz, J., et al., "Gln-Arg192 polymorphism of paraoxonase and coronary heart disease in type 2 diabetes," *Lancet* 346: 869–872 (1995); Serrato, M., et al., "A variant of human paraoxonase/arylesterase (HUMPONA) gene is a risk factor for coronary artery disease," *J. Clin. Invest.* 96: 3005–3008 (1995)). Also, PON-1 has the capacity to destroy certain proinflammatory oxidized phospholipids found in oxidized LDL (Mackness, M. I., et al., "Paraoxonase prevents accumulation of lipoperoxides in low-density lipoprotein," *FEBS Lett* 286: 152–154 (1991); Watson, A. D., et al., "Protective effect of HDL associated paraoxonase-inhibition of the biological activity of minimally oxidized low density lipoprotein," *J. Clin. Invest.* 96: 2882–2891 (1995)). Again, there has been no isolation of the mechanism except to suggest that paraoxonase may be involved.

Mackness et al. ("Is Paraoxonase related to Atherosclerosis," *Chem.-Biol. Interactions* 87:161–171 (1993)) discuss the evidence for an anti-oxidative role for paraoxonase. In this paper they investigated the serum paraoxonase activity in two populations prone to developing atherosclerosis, patients having familial hypercholesterolemia (FH) and IDDM (insulin-dependent diabetes mellitus). They showed a statistically significant increase in the percentage of the population in the low paraoxonase activity group in both FH and IDDM, two diseases manifesting a high occurrence of atherosclerosis. In addition, Mackness et al. studied, in an in vitro LDL oxidation model, the possible role of paraoxonase by adding small amounts in the presence of LDL under oxidative conditions. They concluded that paraoxonase is 300 times more active in preventing LDL oxidation than is HDL or its subfractions. However, they conclude that how paraoxonase protects LDL against oxidation in this model has yet to be determined, and several possibilities are discussed.

In genetic studies with mice, PON1 mRNA and protein levels correlate inversely with aortic lesion size (Shih, D. M., et al., "Genetic-dietary regulation of serum paraoxonase expression and its role in atherogenesis in a mouse model," *J. Clin. Invest.* 97: 1630–1639 (1996)). These data suggest that PON-1 activity may bear some relationship to HDL levels and CAD observed in population studies (Tall, A., "Plasma high density lipoproteins: Metabolism and relationship to atherogenesis," *J. Clin. Invest.* 86: 379–384 (1990)).

Familial hypercholesterolemia is a genetic disorder that results in chronically high levels of serum cholesterol, including both HDL and LDL. The disorder is also characterized as an LDL receptor defect. It is autosomal dominant with prevalence estimates of 1 homozygote per million of population. The LDL receptor normally participates in the uptake and subsequent elimination of LDL by hepatocytes. Accumulation of LDL in these patients is a result of the LDL receptor defect. There are definite high-incidence populations due to a founder effect, with French Canadians being the best known. The heterozygotes develop xanthomas at 20–30 years with atherosclerotic heart disease by 40–50 years in males and 50–60 years in females. Homozygotes usually do not survive beyond their thirties, due to cardiac infarctions caused by excessive placque accumulation. They have total cholesterol in the 500–1,000 mg/dl range, develop xanthomas by age 6, and develop symptomatic coronary artery disease by age 10.

Treatment of LDL receptor deficient patients is problematic. Homozygotes do not respond to HMG-CoA reductase inhibitors (they have no functional LDL receptors to upregulate), and heterozygotes respond half as well as normals. Niacin is effective in lowering LDL, but is poorly tolerated. Non-pharmacologic treatment includes weekly plasmapheresis, partial ileal bypass, protocaval shunts, and liver transplants.

There is a clear need for alternative treatments for those patients exhibiting hypercholesterolemia, particularly familial hypercholesterolemia.

SUMMARY OF THE INVENTION

This invention is directed to a method of decreasing atheroma formation in a mammal comprising a pharmaceutically effective amount of PON-1 or its functional equivalent. It is shown herein in an animal model that, surprisingly, PON-1 can act to reduce the area of aortic lesions, which are predictive of future atherosclerotic placques (atheromas). This discovery represents a potential pharmacological treatment for FH that should be beneficial for hypercholesterolemia generally.

It is an object of the invention to provide a method for decreasing atheroma formation in a mammal by administering a pharmaceutically effective amount of PON-1 or its functional equivalent, thereby decreasing the potential for atherosclerosis.

It is another object of the present invention to provide a new treatment for those afflicted with FH.

DETAILED DESCRIPTION OF THE INVENTION

Definitions

Figure 1:
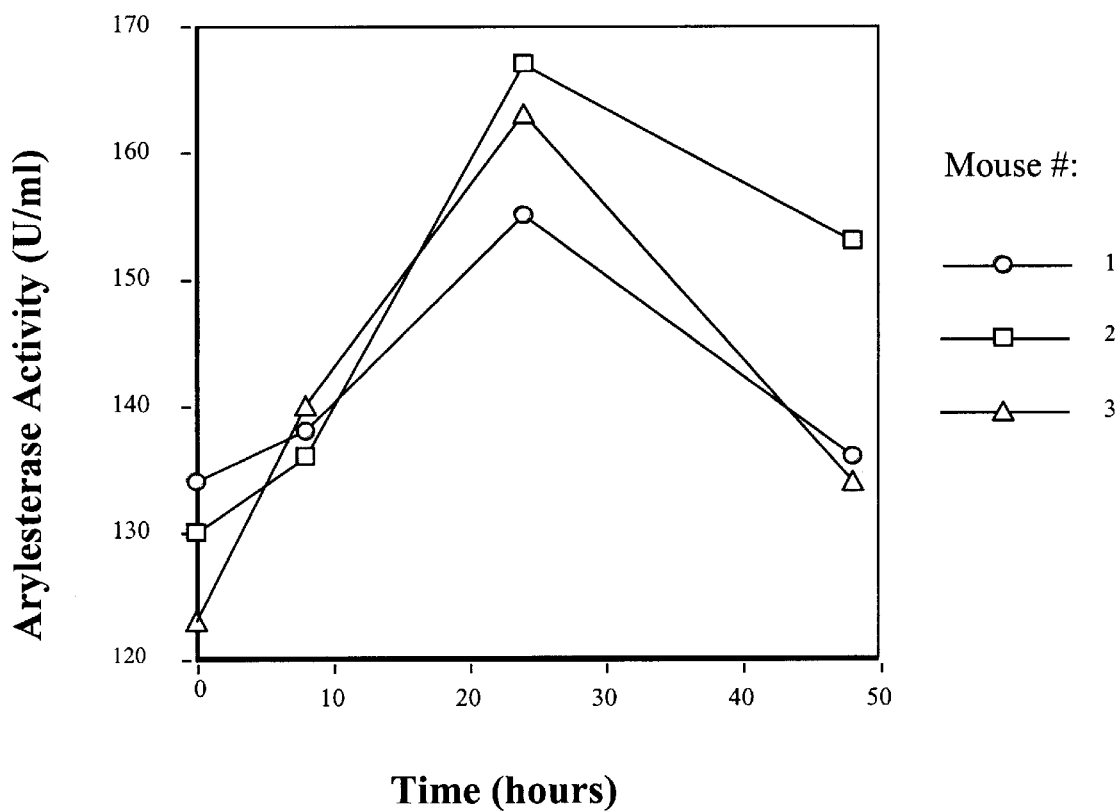
FIG. 1 is a graphical representation of plasma PON-1 (arylesterase assay) activity of LDLR KO mice after receiving an intramuscular (i.m.) injection with 290 units of human PON-1 192Q. Mice were bled at the indicated times (0, 8, 24 and 48 hrs) and PON-1 activities measured.

The term "paraoxonase" refers to any of the three known alleles of the glycoprotein enzyme known as paraoxonase ("PON"), namely PON1, PON2 and PON3, and their naturally-occurring variants. PON isolated from serum is called "serum paraoxonase," also PON-1. PON-1 is the only known allele to be expressed, and is present chiefly in serum. In humans there is a known PON-1 variant at amino acid position 192 called the "192Q" variant that has higher anti-atherogenic activity than do the other variants. In populations of European ancestry, the distribution seems to be polymorphic, with low and high activity sub-forms. 192R is the low-activity variant. The term "PON-1 and its functional equivalents" means any paraoxonase or fragment, deletion variant, substitution variant or derivative having antioxidative activity towards atherogenic lipids at least as effective as native PON-1.

PON-1, as in other proteins, can be varied at specific amino acid residue positions to create other variants of native PON-1 ("muteins"). These variants may have more, less or the same native activity, depending on whether the amino acid substitutions affect the active site, the substrate specificity, the folding of the protein, etc. We prefer conservative modifications and substitutions at other positions of PON-1 (i.e., those that have a minimal effect on the secondary or tertiary structure of the protein). Such conservative substitutions include those described by Dayhoff in *The Atlas of Protein Sequence and Structure* 5 (1978), and by Argos in *EMBO J.*, 8:779–785 (1989). For example, amino acids belonging to one of the following groups represent conservative changes:

ala, pro, gly, gin, asn, ser, thr;

cys, ser, tyr, thr;

val, ile, leu, met, ala, phe;

lys, arg, his;

phe, tyr, trp, his; and asp, glu.

We also prefer modifications or substitutions that do not introduce sites for additional intermolecular crosslinking or incorrect disulfide bond formation. For example, PON-1 is known to have 2 cysteine residues, at wild-type positions 41 and 352 of the mature sequence.

PON-1 can be isolated from human serum or human plasma (Gan, K. N., et al., "Purification of human serum paraoxonase/arylesterase. Evidence for one esterase catalyzing both activities," Drug Metab. Dispos. 19(1):100–6 (1991)) or can be made through recombinant methods. U.S. Pat. Nos. 5,792,639 and 5,629,193 are directed to PON2 genes, proteins and methods of making and using PON-2, and those expression methods are expressly incorporated herein in their entirety. One of ordinary skill is able to use the teachings therein, and combine them with the known sequence of PON1 (SwissProt Accession No. Q16052; ID PON1_HUMAN) to express the PON-1 protein without undue experimentation.

Similarly, if one wished to produce the 192Q or any other variant, a DNA sequence is constructed by isolating or synthesizing a DNA sequence encoding the wild type PON and then changing the native codon for position 192 to a desired codon by site-specific mutagenesis. This technique is well known. gee, e.g., Mark et al. "Site-specific Mutagenesis Of The Human Fibroblast Interferon Gene", *Proc. Natl. Acad. Sci. USA* 81, pp. 5662–66 (1984); and U.S. Pat. No. 4,588,585, incorporated herein by reference.

The biological activity of the PON-1 glycoprotein of this invention can be assayed by any suitable method known in the art. Two methods are disclosed herein, the paraoxonase assay, and the arylesterase assay. (See I. Methods, below).

Pharmaceutical Compositions

The PON-1 protein (also referred to herein as "active compounds") of the invention can be incorporated into pharmaceutical compositions suitable for administration. Such compositions typically comprise the protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. For instance, it is known that PON-1 is a calcium-dependent protein, having several calcium binding loops (Sorenson et al., "Reconsideration of the catalytic center and mechanism of mammalian paraoxonase/arylesterase," *Proc. Natl. Acad. Sci. USA* 92: 7187–7191 (1995)). Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid, tocopherol or sodium bisulfite; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a PON-1 protein or anti-PON-1 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. Stabilizers such as albumin, HDL or a sugar such as sucrose, or calcium ions may also be included to increase the shelf-life of the protein.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch, a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

General guidance regarding dosage and compositions is available in *Remington's Pharmacautical Science* by E. W. Martin, hereby incorporated by reference.

The invention is further directed to a method of diagnosing predisposition to hypercholesterolemia by assessing the level of native circulating PON-1 in a mammal. The results of the animal testing presented herein show that PON-1 administration can reduce, by a surprising factor, the build-up of fatty streaks in mouse aortic tissues. Thus, detection and monitoring of PON-1 levels in a mammal may be diagnostic of subsequent atheroma formation, which is predictive of atherosclerosis. Assays such as are presented here for paraoxonase or arylesterase may be the basis of such a diagnostic method. The method may take into account the genetic differences between sub-populations which express phenotypic variations in PON-1 which are correlated with higher than normal cardiovascular events. For instance, the PON-1 192Q phenotype has been correlated with higher paraoxonase activity than the 192R phenotype. It would be expected that an assay may be based on measuring either phenotype separately, and/or the ratio of these two phenotypes present in an individual in order to predict their individual susceptibility to atherosclerosis.

Also contemplated is the use of DNA sequences encoding PON-1 in gene therapy applications. Gene therapy applications contemplated include treatment of those diseases in which PON-1 is expected to provide an effective therapy due to its ability to decrease lipid oxidation such as atherosclerosis, and diseases that are otherwise responsive to lipid oxidation levels. Familial hypercholesterolemia, which is manifested by the lack of expression of LDL receptors, is one such disease that results in very high levels of circulating cholesterol, triglycerides and related lipids.

Local delivery of PON-1 using gene therapy may provide the therapeutic agent to the target area. Both in vitro and in vivo gene therapy methodologies are contemplated. Several methods for transferring potentially therapeutic genes to defined cell populations are known. See, e.g., Mulligan, "The Basic Science Of Gene Therapy", *Science*, 260: 926–31 (1993). These methods include:

1) Direct gene transfer. See, e.g., Wolff et al., "Direct Gene transfer Into Mouse Muscle In Vivo", *Science*, 247:1465–68 (1990);

2) Liposome-mediated DNA transfer. See, e.g., Caplen at al., "Liposome-mediated CFTR Gene Transfer To The Nasal Epithelium Of Patients With Cystic Fibrosis", *Nature Med.* 3: 39–46 (1995); Crystal, "The Gene As A Drug", *Nature Med.* 1:15–17 (1995); Gao and Huang, "A Novel Cationic Liposome Reagent For Efficient Transfection Of Mammalian Cells", *Biochem. Biophys. Res. Comm.*, 179:280–85 (1991);

3) Retrovirus-mediated DNA transfer. See, e.g., Kay et al., "In Vivo Gene Therapy Of Hemophilia B: Sustained Partial Correction In Factor IX-Deficient Dogs", *Science*, 262:117–19 (1993); Anderson, "Human Gene Therapy", *Science*, 256:808–13 (1992).

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses As Vectors For Gene Therapy", *Gene Therapy*, 1:367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity.

Adenoviruses have the advantage that they have a broad host range, can infect quiescent or terminally differentiated cells, such as neurons or hepatocytes, and appear essentially non-oncogenic. See, e.g., Ali et al., supra, p. 367. Adenoviruses do not appear to integrate into the host genome. Because they exist extrachromosomally, the risk of insertional mutagenesis is greatly reduced. Ali et al., supra, p. 373.

Adeno-associated viruses exhibit similar advantages as adenoviral-based vectors. However, AAVs exhibit site-specific integration on human chromosome 19. Ali et al., supra, p. 377.

In a preferred embodiment, the PON-1 encoding DNA of this invention is used in gene therapy for lipid-based disorders such as FH, and cardiovascular complications arising from other disorders such as non-insulin dependent diabetes mellitus.

According to this embodiment, gene therapy with DNA encoding PON-1 or muteins of this invention is provided to a patient in need thereof, concurrent with, or immediately after diagnosis.

The skilled artisan will appreciate that any suitable gene therapy vector containing PON-1 DNA or DNA of muteins of PON-1 may be used in accordance with this embodiment. The techniques for constructing such a vector are known. See, e.g., Anderson, W. F., "Human Gene Therapy," *Nature*, 392 25–30 (1998); Verma, I. M., and Somia, N., "Gene Therapy—Promises, Problems, and Prospects," *Nature*, 389 239–242 (1998). Introduction of the PON-1 DNA-containing vector to the target site may be accomplished using known techniques. This invention is further illustrated by the following examples, which should not be construed to limit the invention, but serve to support it. The content of all patents, patent applications and references referred to herein are hereby incorporated in their entirety.

EXAMPLES

I. Methods

Mice and Diet. The LDLR KO mouse model is a recognized animal model for predicting pharmacological activity for pharmaceutical candidates in the field of atherogenesis. Their LDL receptors, necessary for removal of atherogenic LDL, have been deleted by homologous recombination (Ishibashi S., et al., "Hypercholesterolemia in low density lipoprotein receptor knockout mice and its reversal by adenovirus-mediated gene delivery," J. Clin. Invest. 92(2) :883–893 (1993)). These mice are particularly susceptible to atheroma formation (fatty streaks) in their primary arteries if fed a high-fat diet. Two month-old female LDL receptor knockout (LDLR KO) mice were purchased from Jackson Laboratory (Bar Harbor, Me.) and maintained on a 6% fat chow diet (Harlan Teklad, Madison, Wis.). For the PON replacement study, 50 female LDLR KO mice, at 3 months of age, were divided into the following 5 groups with 10 mice/group:

Group 1: baseline group, sacrificed on day 0.

Group 2: 4-week chow group, these mice were fed the 6% fat chow diet and sacrificed on day 28. PON-1 activities were measured by paraoxonase assay in groups 4 and 5.

Group 3: 4-week high fat diet group, these mice were fed the high fat diet for 4 weeks and sacrificed on day 28.

Group 4: 4-week high fat diet plus buffer injection, these mice were fed the high fat diet for 4 weeks (day 1 to day 28) and received 80 μl of buffer injections via i.m. on day 1, 3, 6, 8, 10, 13, 15, and 17. The mice then received 80 μl of buffer injections via i.p. on day 20, 21, 22, 23, 24, 25, 26, 27. The mice were then sacrificed on day 28.

Group 5: 4-week high fat diet plus PON injection, these mice were fed the high-fat diet for 4 weeks (day 1 to day 28) and received 80 μl (800 μg, 290 units of paraoxonase activity) of human PON-1 192Q (PON-1 was purified from human plasma donors homozygous for the 192Q mutation, using the method described by Bert LA Du (Gan, K. N., et al., "Purification of human serum paraoxonase/arylesterase. Evidence for one esterase catalyzing both activities," *Drug Metab. Dispos.* 19(1):100–106 (1991)) injections via i.m. on day 1, 3, 6, 8, 10, 13, 15, and 17. The mice then received 80 μl of human PON-1 192Q injections via i.p. on day 20, 21, 22, 23, 24, 25, 26, 27. The mice were then sacrificed on day 28.

The high-fat diet contained 15.75% fat, 1.25% cholesterol and 0.5% sodium cholate (Teklad, Madison, Wis.). For groups 4 and 5, plasma PON-1 activities were measured on both day 7 (24 hours after an i.m. injection) and day 28 at sacrifice (24 hours after an i.p. injection). For groups 1, 2, and 3, PON-1 activities were measured in plasma samples collected at sacrifice. At sacrifice, the mice were fasted overnight and killed. Blood, hearts, and livers were collected for further analysis.

PON-1 activities and lipid assays. PON-1 activities were measured either by paraoxonase assay using the organophosphate paraoxon as the substrate (Furlong, C. E. et al., "Spectrophotometric assays for the enzymatic hydrolysis of the active metabolites of chlorpyrifos and parathion by plasma paraoxonase/arylesterase," *Anal. Biochem.* 180: 242–247 (1989)) or by arylesterase assay using phenyl acetate as the substrate (Furlong, C. E., et al., "Role of genetic polymorphism of human plasma paraoxonase/arylesterase in hydrolysis of the insecticide metabolites chlorpyrifos oxon and paraoxon," *Am. J. Hum. Genet.* 43:230–238 (1988)). Briefly, for the paraoxonase assay, 5 μl of plasma was mixed with the substrate solution containing 1.2 mM of paraoxon, 2.0 M NaCl, 0.1 M Tris HCl pH 8.5 and 2.0 mM $CaCl_2$. The production of p-nitrophenol was measured, at room temperature, as change in absorbance (O.D.) at 405 nm over 5 minutes. A standard curve was also constructed by measuring $O.D._{405}$ of various concentrations of p-nitrophenol. One unit of paraoxonase activity is defined as 1 nmole of p-nitrophenol produced/min. For arylesterase assay, 1 μl of plasma was mixed with 1 ml of substrate solution containing 3.26 mM phenylacetate, 9.0 mM Tris HCl pH 8.0, and 0.9 mM $CaCl_2$. The production of phenol was measured, at room temperature, as change in absorbance (O.D.) at 270 nm over 2 minutes. The arylesterase activity was then calculated using the molar exinction coefficient for phenol ($1,310\ M^{-1}\ cm^{-1}$). One unit of arylesterase activity is defined as 1 μmole phenol produced/min. For all of the groups, plasma total cholesterol, HDL cholesterol, VLDL/LDL cholesterol, and triglycerides were measured in plasma samples collected at sacrifice using enzymatic procedures employing enzymatic end points (Mehrabian, M., et al., "Influence of the apoA-II gene locus on HDL levels and fatty streak development in mice," *Arterioscler. Thromb.* 13:1–10 (1993)).

Aortic lesion measurements. Briefly, the use of aortic lesion measurements requires that, at sacrifice, the upper portion of the heart and proximal aorta is obtained and embedded in OCT compound (Tissue-Tek OCT Compound—Sakura Finetek USA Inc., Torrence, Calif.) and frozen. Every other 10-μm thick cryosection, beginning where the aortic valves appear, is collected for a distance of about 500 μm. These sections are stained with oil red O (Oil Red O, Sigma Chemical Company, St. Louis, Mo.) and counter-stained with hematoxylin (Hematoxylin aqueous formula, Biomeda Corp., Foster City, Calif.) and Fast Green (Fast Green FCF, Sigma, St. Louis, Mo.). The lipid containing areas on 25 sections are determined using a microscope eyepiece grid. Mean lesion area/section are then calculated (Mehrabian, M., et al., "Influence of the apoA-II gene locus on HDL levels and fatty streak development in mice," Arterioscler. Thromb. 13: 1–10 (1993)).

Western blot analysis. Various amounts of purified human PON-1 192Q (400,200, 100, 50 ng/lane) and 1 μl of mouse HDL (equivalent to 6 μl of mouse plasma) were loaded on denaturing polyacrylamide gel for electrophoresis (denaturing agent used: 2×buffer: 0.5 M Tris-HCl, pH6.8, 2.5 ml; glycerol, 2 ml; 10% SDS, 4 ml; 0.1% bromophenol blue, 0.5 ml; beta-mercaptoethanol,0.5 ml; water to 10.0 ml). The fractionated proteins were then transferred onto nitrocellulose paper (Hybond-ECL nitrocellulose, Amersham, Buckinghamshire,UK). Four of such identical nitrocellulose blots were than incubated for 1 hour with one of the following solutions: (1) 1:500 dilution of pooled plasma from mice injected with buffer after 4 weeks of injection, (2) 1:500 dilution of pooled plasma from mice injected with human PON-1 192Q after 4 weeks of injection, (3) 1:500 dilution of pooled plasma from mice injected with human PON-1 192Q after 1 week of injection, (4), 1:1000 dilution of a rabbit antibody against mouse PON-1 (rabbit anti-mouse PON-1: was generated using recombinant mouse PON-1 expressed in E. coli at UCLA by Diana Shih and Ling-jie Gu, unpublished results). The blots were then washed with PBS containing 0.1% Tween-20 and then incubated for 1 hour with anti-rabbit IgG secondary antibodies conjugated with HRP (Amersham, Buckinghamshire, UK). The blots were then washed and the image was visualized using the ECL Western blotting detection reagents from Amersham (Amersham, Life Science, Inc., Arlington Heights, Ill.).

II. EXAMPLES

Example 1.
Time Course Study of Plasma PON-1 Activity in LDLR KO Mice Injected with Human PON-1 192Q Three female LDLR KO mice, maintained on chow diet, were each injected i.m. with 290 units of human PON-1 192Q. Blood samples were collected immediately before the injection (time 0) and 8, 24, and 48 hours after the injection. Plasma PON-1 activities were then measured using arylesterase assay. As shown in FIG. 1, the mean plasma PON-1 activity at 8, 24, and 48 hr after injection was 107%, 125%, 109% that of time 0 (time 0 vs. 24-hr, p=0.003). Our data indicate that i.m. injection is an effective way to deliver PON-1 into mice. However, the increases in PON-1 activities in these mice were smaller than what we have expected.

Example 2.
PON-1 192Q Replacement Study

The experimental design was previously described in Methods. For Group 4 (4-week high fat diet plus buffer injection) and Group 5 (4 week high-fat diet plus 290 units human PON-1 192Q injection), plasma PON-1 activities were measured on day 7, 24 hr after the third i.m. injection. At day 7 there were 10 mice in each group; values shown are averages from two independent paraoxonase assays. At day 28, there were 9 mice in each group; paraoxonase assay.

Figure 2A:
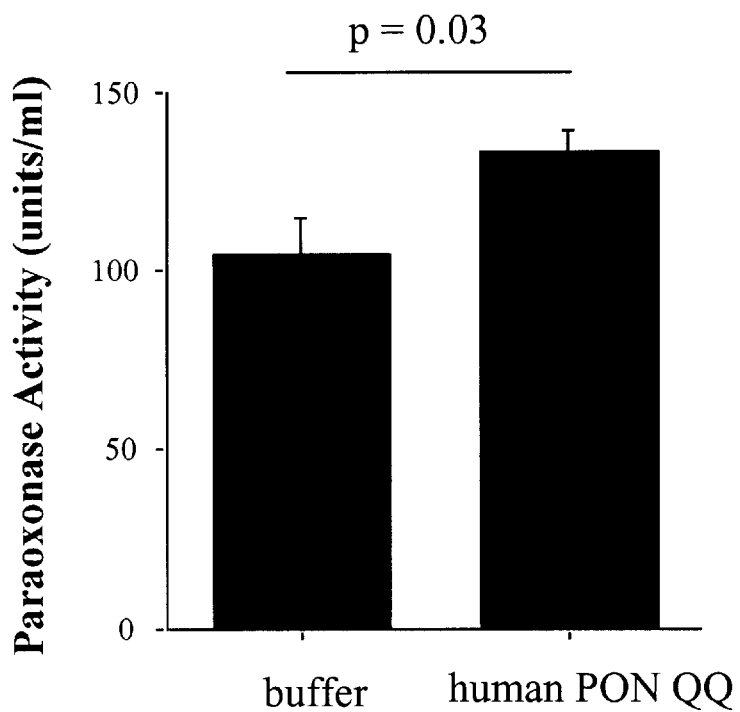
FIGS. 2A and 2B are bar graphs showing the amount of human PON-1 present in mouse serum 24 hours after injection, either on day 7 (FIG. 2A) or on day 28 (FIG. 2B). Control mice received buffer.
Figure 2B:
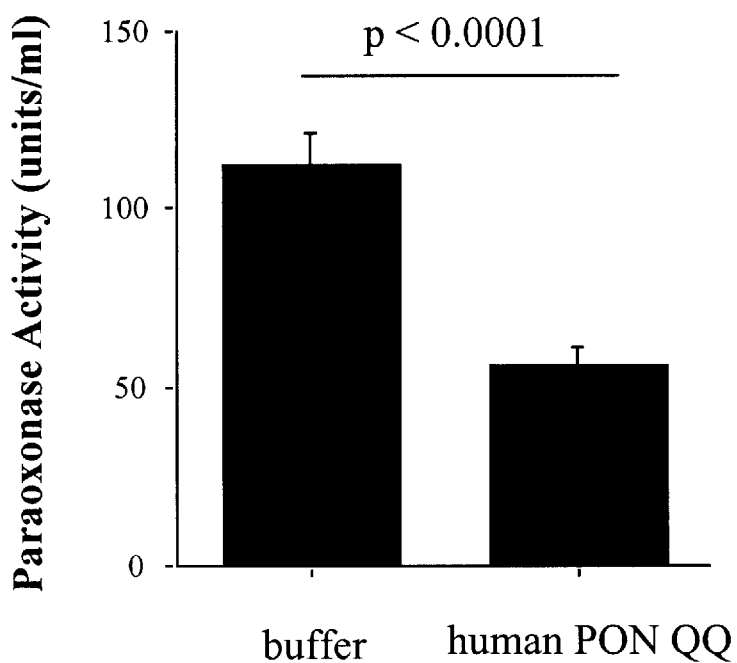
Figure 3A:
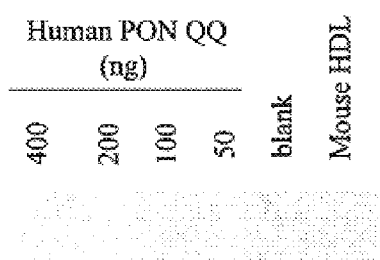
FIGS. 3A through D are Western Blots showing the generation of anti human PON-1 antibodies in mice treated with human PON-1, over the course of the study.
Figure 3B:
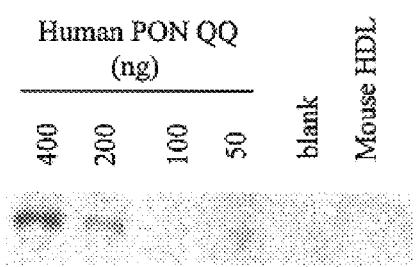
Figure 3C:
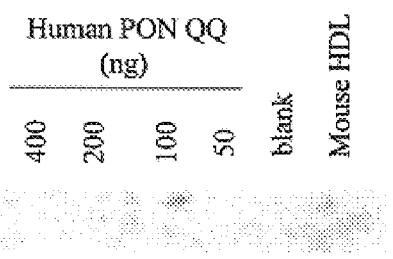
Figure 3D:
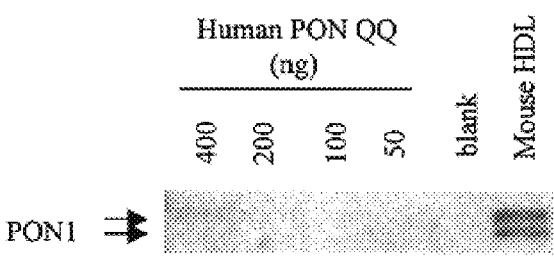

As shown in FIGS. 2A and 2B, we found that, on day 7, the high-fat diet plus PON-1 injection group exhibited 27% higher PON-1 activities as compared to the high fat plus buffer injection group (p=0.03) (FIG. 2A). However, on day 28 (FIG. 2B), we found that the high fat diet plus PON-1 injection group had only 50% of the PON-1 activities as compared to those of the high-fat plus buffer injection group (p<0.0001). We postulated that the reduction of PON-1 activities in the PON-1 injected group on day 28 was likely caused by an immune response in the mice toward the injected human PON-1 192Q.

Example 3.
Detection of Anti-human PON-1 Antibodies in LDLR KO Mice Injected with Human PON-1.

Various amounts of purified human PON-1 192Q (400, 200, 100, 50 ng/ane) and 1 μl of mouse HDL (equivalent to 6 μl of mouse plasma) were loaded on denaturing polyacrylamide gel for electrophoresis. The fractionated proteins were then transferred onto nitrocellulose paper. Specifically with regard to FIGS. 3A through D, four of these identical nitrocellulose blots were then incubated for 1 hour with one of the following solutions: panel A, 1:500 dilution of pooled plasma from mice injected with buffer after 4 weeks of buffer injection; panel B, 1:500 dilution of pooled plasma from mice injected with human PON-1 192Q after 4 weeks of injection; panel C, 1:500 dilution of pooled plasma from mice injected with human PON-1 192Q after 1 week of injection; and panel D, 1:1000 dilution of a rabbit antibody against mouse PON-1. The blots were then washed with PBS containing 0.1% of Tween-20 and incubated for 1 hour with secondary antibodies conjugated with HRP. The blots were then washed and the image was visualized using the ECL technique. As shown in panel A, the 4-week buffer-injected mice did not have antibodies against human PON-1 in their plasma, while the 4-week PON-1-injected mice contain antibodies against human PON-1 in their plasma (panel B). However, these antibodies did not cross react with the mouse PON (Panel B). We did not detect any anti-human PON-1 antibodies in the pooled plasma of 1-week PON-1-injected mice (panel C). As shown in panel D, a rabbit anti-mouse PON-1 antibody detected both the mouse PON-1 and, to a lesser extent, the human PON-1.

It is unlikely that the reduction of PON-1 activities in the PON-1 injected animals on day 28 is directly caused by the interaction between the mouse PON-1 and the antibodies since the antibodies against human PON-1 did not cross react with the mouse PON-1 protein. Since the human PON-1 is likely to reside on the same HDL particles as the mouse PON-1, recognition of the PON-1 containing HDL particles by the antibodies may enhance the clearance of these HDL particles, thus causing the removal of mouse PON-1 on the same particles.

Example 4
Livid Levels

Lipid levels of plasma samples collected at sacrifice were examined. As shown in Table 1, there were no significant differences in plasma lipid levels between the 4-week high-fat plus buffer-injected group and the 4-week high fat-group. Interestingly, as compared to the buffer-injected mice, the PON-1-injected mice had a moderate decrease in both total cholesterol (p=0.04) and VLDL/LDL cholesterol (p=0.04) levels, a moderate increase in triglycerides (p=0.005), and no difference in HDL cholesterol level. Therefore, the PON-1-injected mice had a less atherogenic lipid profile as compared to the buffer-injected group.

TABLE 1

Plasma PON-1 activities and lipid levels of LDLR KO mice at sacrifice

| | PON-1 activity[1] | Total Cholesterol[2] | VLDL/LDL Cholesterol[2] | HDL Cholesterol[2] | Trigly-cerides[2] |
|---|---|---|---|---|---|
| Base line | 329 ± 21 | 291 ± 15 | 206 ± 17 | 86 ± 3 | 162 ± 16 |
| 4-Week Chow | 420 ± 11 | 332 ± 10 | 230 ± 10 | 101 ± 2 | 318 ± 25 |
| 4-Week HF[3] | 105 ± 6 | 2315 ± 175 | 2289 ± 174 | 27 ± 3 | 44 ± 11 |
| 4-Week HF[3] + Buffer | 112 ± 9 | 2213 ± 145 | 2190 ± 145 | 23 ± 2 | 26 ± 4 |
| 4-Week HF[3] + PON-1 | 56 ± 5 | 1862 ± 63 | 1836 ± 62 | 26 ± 2 | 44 ± 4 |

[1]Values shown are mean ± S.E. of 9 or 10 animals in each group. The units are units of paraoxonase activity/ml plasma.
[2]Values shown are mean ± S.E. of 9 or 10 animals in each group. The units are mg/dL.
[3]HF means high fat diet.

Example 5
Aortic Lesions

Figure 4:
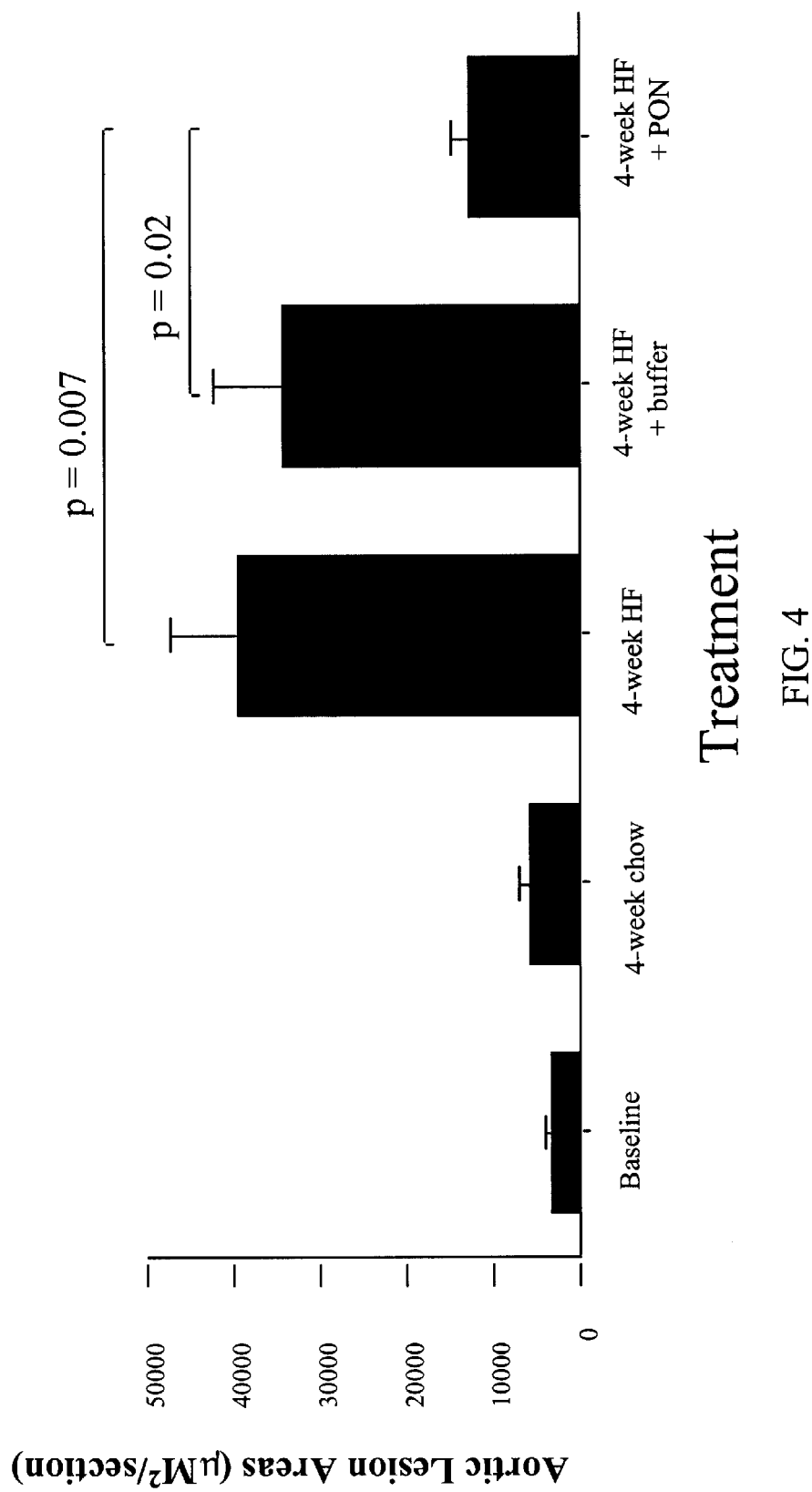
FIG. 4 is a bar graph comparing aortic lesion size in LDLR KO mice in PON-1 treated v. control-treated groups.

We then examined the aortic fatty streak formation in these mice. Three-month old female LDLR KO mice (10 mice/group) were either sacrificed at time 0 (baseline group), fed the chow diet for 4 weeks (4-week chow), fed the high-fat diet for 4 weeks (4-week HF), fed the high fat diet plus buffer injections (4-week HF +buffer), or fed the high-fat diet plus human PON-1 192Q injections (4-week HF +PON). At the end of 4-week treatments, mice were sacrificed. The hearts were collected and aortic lesion areas were scored. For Group 4 (4-week HF +buffer) and Group 5 (4-week HF+PON), the lesion sizes were scored once in a non-blind and once in a blind fashion to avoid bias. The scores from both times were very similar. We found no significant difference in aortic lesion sizes between the 4-week high-fat and the 4-week high-fat plus buffer injection group (FIG. 4). From the non-blind scoring, the mean lesion sizes of the buffer injected (Group 4) and PON-1-injected (Group 5) groups were 34222±8008 and 12864±1985 mm$^2$/section, respectively. From the blind scoring, the mean lesion sizes of the buffer injected and PON-1-injected groups were 32422±7470 and 13383±1850 mm$^2$/section, respectively. Therefore, we obtained very similar results using either blind or non-blind methods, demonstrating that the 4-week high-fat plus PON-1 192Q injection group had significantly less aortic lesion area than both the 4-week high-fat plus buffer-injected group and the 4-week high-fat group (FIG. 4). The results suggest that PON-1 replacement is an effective way to reduce aortic fatty streak lesion in the LDLR KO mice.

In summary, it was found that the PON-1 192Q-injected mice had elevated PON-1 activities on day 7, and lower levels of PON-1 activities on day 28 as compared to the buffer-injected mice. However, when aortic lesion formation was examined on day 28, a surprizingly large 60% (approximate) reduction in aortic lesion size was found in PON-1 192Q-injected mice as compared to the buffer-injected mice. Possible explanations for the low PON-1 activity levels in PON-1-treated mice on day 28 are as follows: First, the generation and the titer of antibodies against human PON-1 192Q in PON-1 injected mice probably started late and remained low until the end of the experiment. Therefore, for most of the time during the study, the injected PON-1 192Q was effective in preventing LDL oxidation and, thus, atherosclerosis. Second, if one assumes that PON-1 is most effective in preventing the initiation of atherosclerosis, that is prevention of LDL oxidation and therefore prevention of inflammatory response and reduced recruitment of monocytes into subendothelial cells (Mackness, M. I., et al, supra; Watson, A. D., et al., supra; Shih, D. M., et al., "Mice lacking serum paraoxonase are susceptible to organophosphate toxicity and atherosclerosis," Nature 394:284–287 (1998)), then the PON replacement might have been most effective during the first 2 weeks of the study rather than the last 2 weeks of the study. Therefore, even though PON-1-injected mice had less PON-1 activity than the buffer-injected mice at the end of the 28-day experiment, they still developed less aortic lesions.

Those skilled in the art will be able to recognize, or be able to ascertain using no more than routine experimentation, many equivalents to the specific embodiments of the invention described herein. For instance, PON-2 and PON-3 may have antioxidant activity similar to that of PON-1, and may be equally useful in the method of this invention. Also, other deletion or substitution mutations may provide similar functional equivalents. Such equivalents are intended to be encompassed by the spirit and scope of the following claims.

I claim:

1. A method of decreasing atheroma formation in a mammal comprising administering a pharmaceutically effective amount of PON-1 polypeptide, wherein reduction in aortic lesion formation is taken as a measure of decreased atheroma formation.

2. The method of claim 1 wherein said effective amount ranges from about 0.1 μg/kg of body weight to about 100 mg/kg.

3. The method of claim 1 wherein said PON-1 comprises human plasma-derived PON-1.

4. The method of claim 1 wherein said PON-1 comprises human serum-derived PON-1.

5. The method of claim 1 wherein said PON-1 comprises PON-1 192Q.

6. The method of claim 1 wherein said PON-1 is in a pharmaceutically acceptable carrier.

7. A method of decreasing atheroma formation in a mammal comprising administering a pharmaceutically effective amount of PON-1 polypeptide that is recognized by a PON-1-specific antibody, wherein reduction in aortic lesion formation is taken as a measure of decreased atheroma formation.

8. The method of claim 7 wherein said polypeptide has paraoxonase and arylesterase activity and specifically binds apoJ.

9. The method of claim 7 wherein said polypeptide is in a pharmaceutically acceptable carrier.

10. The method of claim 7 wherein said polypeptide is human plasma-derived PON-1.

11. The method of claim 7 wherein said polypeptide is human serum-derived PON-1.

* * * * *